(12) United States Patent
Cytryn

(10) Patent No.: US 11,324,629 B2
(45) Date of Patent: May 10, 2022

(54) VOCAL STRENGTHENING APPARATUS

(71) Applicant: SINGING STRAW LLC, San Francisco, CA (US)

(72) Inventor: Whitney Cytryn, San Rafael, CA (US)

(73) Assignee: SINGING STRAW LLC, San Francisco, CA (US)

( * ) Notice: Subject to any disclaimer, the term of this patent is extended or adjusted under 35 U.S.C. 154(b) by 0 days.

(21) Appl. No.: 16/532,337

(22) Filed: Aug. 5, 2019

(65) Prior Publication Data

US 2020/0315840 A1 Oct. 8, 2020

Related U.S. Application Data

(60) Provisional application No. 62/829,734, filed on Apr. 5, 2019.

(51) Int. Cl.
*A61F 5/58* (2006.01)

(52) U.S. Cl.
CPC ...................... *A61F 5/58* (2013.01)

(58) Field of Classification Search
CPC .... A61F 5/58; B27K 9/007; A47G 21/18–189
See application file for complete search history.

(56) References Cited

U.S. PATENT DOCUMENTS

| 10,694,922 | B1 * | 6/2020 | Audibert | A47L 15/505 |
| D899,772 | S * | 10/2020 | Kauffman | D3/294 |
| 2015/0014431 | A1 * | 1/2015 | Whittaker | A47G 21/182 |
| | | | | 239/33 |
| 2015/0190004 | A1 * | 7/2015 | Chang | A47G 21/18 |
| | | | | 239/33 |
| 2015/0320246 | A1 * | 11/2015 | Jorge | A47G 19/2222 |
| | | | | 220/592.17 |
| 2019/0099025 | A1 * | 4/2019 | Rieger | A47G 21/182 |
| 2019/0105534 | A1 * | 4/2019 | Lundquist | A61M 16/0006 |

OTHER PUBLICATIONS

Oovo Straw (https://oovostraw.com/about-oovo; backdated to at least Apr. 1, 2019 via the Wayback Machine: https://web.archive.org/web/20190401165305if_/https://oovostraw.com/about-oovo. (Year: 2019).*
The voice straw: https://voicestraw.com/.
The voice straw: https://voicestraw.com/products/the-voice-straw.
Oovo straw: https://oovostraw.com/.
Oovo straw: https//oovostraw.com/product/oovo-care-kit.
Oovo straw as of Apr. 1, 2019: https://web.archive.org/web/20190401074553/https:/oovostraw.com/product/oovo-straw.
Smith et al., "Characterziation of Flow-Resistant Tubes used for Semi-Occluded Vocal Tract Voice Training and Therapy," J. Voice, Author Manuscript, available in PMC Jan. 1, 2018, 16 pages.

* cited by examiner

*Primary Examiner* — Thaddeus B Cox
(74) *Attorney, Agent, or Firm* — Greenberg Traurig, LLP

(57) ABSTRACT

Apparatuses for use in straw phonation are provided herein. These apparatuses are typically reusable. Kits comprising these apparatuses are also provided which allow the apparatuses to be stored safely for repeated use throughout the day as required. Additionally, the present disclosure is related to methods of practicing straw phonation with the apparatuses described herein.

7 Claims, 1 Drawing Sheet

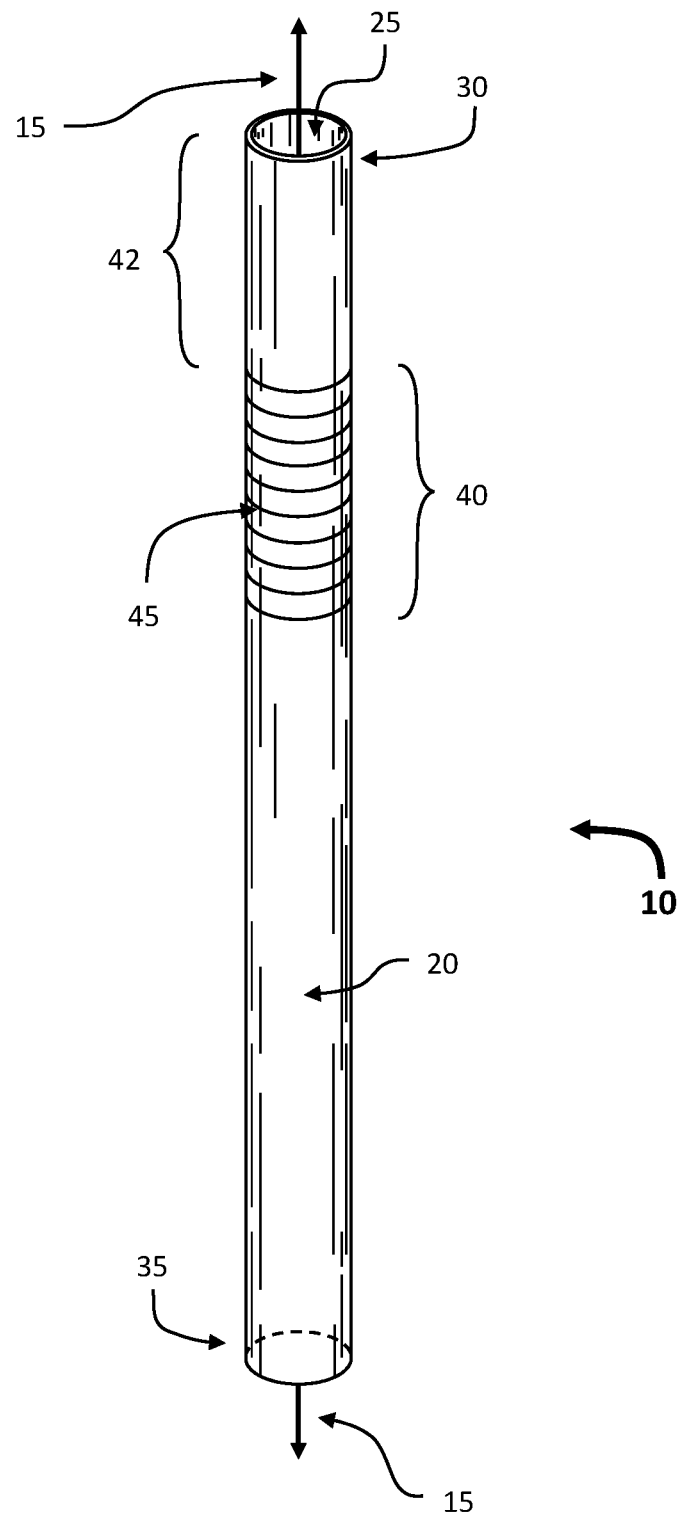

VOCAL STRENGTHENING APPARATUS

CROSS REFERENCE TO RELATED APPLICATIONS

The present application claims priority to U.S. App. No. 62/829,734, filed Apr. 5, 2019, the contents of which are hereby incorporated by reference in their entirety.

FIELD OF INVENTION

The present invention is directed to apparatuses used to help strengthen develop the ease and efficiency of a user's vocalization. The apparatus is typically a hollow cylinder. A user inserts a distal end of the hollow cylinder into their mouth and makes sounds in order to provide benefit to their vocal folds.

BACKGROUND OF INVENTION

Straw phonation is a method of exercising the vocal folds in order to improve the voice. This is achieved by the alteration of pressure in the vocal tract. Pressure in the vocal tract is a large contributor to vocal fold vibration and therefore voice balance, efficiency, and strength. Partially closed mouths (or mouths wrapped around an apparatus such as a straw or hollow cylinder) cause increased supraglottal pressure in the vocal tract thereby balancing the subglottal pressure and encouraging a more optimal vocal fold closure pattern, thereby reducing impact and effort in vocal fold vibration. Partially closed mouths reflect air flow that would typically exit the mouth returning that air flow back to the vocal folds. This back pressure helps align the vocal folds in a more optimal position. Vocalization with a partially closed mouth also helps to relax and open the pharynx, lower the larynx, and reduce external tension. Routinely exercising the vocal folds in this way helps train the vocal folds to vibrate in a more efficient and balanced pattern with less effort and more ease. By making sound throughout the vocal range with a straw inserted in the mouth, it is possible to train one's voice to regularly achieve this more efficient vocal fold positioning.

The training has tremendous benefit to a variety of fields. For example, straw phonation may be used by singers of all competencies, rehabilitation after vocal trauma or injury, or simply to improve vocal stamina. Such training may help reduce inflammation from overuse and relieve tension in the vocal tract. Accordingly, straw phonation is particularly useful for people with occupations requiring routine use of their voice such as realtors, teachers, and sales professionals. Additionally, straw phonation and the sound exercises associated therewith may focus on specific skill sets a user would like to exercise such as belting, transitioning, riffing, extending range, developing vibrato, extending balance, and extending strength.

Typically, straw phonation is used with plastic straws which must be constantly replenished bringing about a variety of issues including sanitary, economic, availability, and environmental. For example, plastic straws may be unsanitary and difficult to keep clean. Additionally, they may be lost easily. Moreover, these straws are often easily bent or flattened at the distal end thereby affect their use as an apparatus for straw phonation.

It is therefore an object of the present disclosure to provide apparatuses, kits, and methods of straw phonation that overcome these issues.

SUMMARY

In accordance with the foregoing objectives and others, disclosed herein are apparatuses for use in these straw phonation vocal exercises. The apparatuses described herein are designed to help singers, vocalists, and voice users (e.g., realtors, teachers, sales professionals, etc.) strengthen, train and develop their voice using straw phonation.

Typically, the apparatus may be composed of a unitary piece of material formed as a hollow cylinder;
wherein the maximum inner diameter of the hollow cylinder is less than 8 mm (e.g., less than 6 mm, less than 5 mm, etc.);
the outer diameter of the hollow cylinder is dimensioned to be gripped by a user at a location away from one or both of the distal ends of the hollow cylinder between a thumb and index finger of the user;
one of the distal ends is dimensioned to be inserted into the mouth of the user; and
a portion of the outer diameter comprises a roughened surface for the gripping by the user.

In certain embodiments, the apparatus may be composed of a unitary piece of stainless steel formed as a hollow cylinder;
wherein the maximum inner diameter is between 2 and 6 mm (e.g., 3 mm);
the outer diameter of the hollow cylinder is between 4 and 7 mm (e.g., 5 mm); and
a portion of the outer diameter comprises a one or more five or more (e.g., five, six, seven, eight, nine, ten, eleven, twelve, thirteen, fourteen, fifteen, etc.) concentric scored grips that extend more than 90% (e.g., more than 95%, etc.) or entirely around the periphery of the hollow cylinder in a plane perpendicular to the longitudinal axis of the hollow cylinder.

Kits for the apparatuses are also provided which may comprise:
  (a) one or more (e.g., two or more, three or more, etc.) of the apparatuses described herein; and
  (b) a container capable of storing the one or more apparatuses in a chamber.

In some embodiments, one or more of the apparatus do not comprise the roughened surface. In some embodiments, each of the apparatuses in the do not comprise the roughened surface. In other embodiments, one or more of the apparatuses comprise a roughened surface. In certain embodiments, one or more of the apparatuses comprise a roughened surface. The roughened surface may comprise one or more or five or more (e.g., five, six, seven, eight, nine, ten, eleven, twelve, thirteen, fourteen, fifteen, etc.) concentric scored grips that extend more than 90% (e.g., more than 95%, etc.) or entirely around the periphery of the hollow cylinder in a plane perpendicular to the longitudinal axis of the hollow cylinder. In some embodiments, each of the apparatuses in the kit comprises concentric scored grips. In certain implementations, the kit further comprises one or more brushes for cleaning the apparatuses (e.g., cleaning the inner surface of the hollow cylinder. In some embodiments the kit comprises three apparatuses and a brush for cleaning the apparatuses after use (e.g., a twisted wire brush, etc.). In certain embodiments, the brush is dimensioned to be inserted into at least one or all of the apparatuses of the kit to clean the interior surface. In various implementations, the kit comprises three apparatuses each with an inner diameter of 3 mm. In other embodiments, the kit comprises a first apparatus with an inner diameter of 2 mm, a second apparatus with an inner diameter of 3 mm, and a third apparatus with an inner diameter of 4 mm.

Methods of exercising the voice of a user (e.g., aligning the vocal folds of a user, etc.) are provided as well. The method may comprise:

(a) inserting the distal end of an apparatus described herein into the mouth of a user;
(b) forming a seal between the outer periphery of said apparatus and the mouth; and
(c) creating sound with the vocal folds of the user while the apparatus is positioned in the mouth.

BRIEF DESCRIPTION OF FIGURES

FIG. 1 is a perspective view of an exemplary apparatus disclosed herein.

DETAILED DESCRIPTION

Detailed embodiments of the present disclosure are disclosed herein; however, it is to be understood that the disclosed embodiments are merely illustrative of the invention that may be embodied in various forms. In addition, each of the examples given in connection with the various embodiments of the invention is intended to be illustrative, and not restrictive.

All terms used herein are intended to have their ordinary meaning in the art unless otherwise provided.

As used herein, "a" or "an" shall mean one or more. As used herein when used in conjunction with the word "comprising," the words "a" or "an" mean one or more than one. As used herein "another" means at least a second or more.

As used herein, all ranges of numeric values include the endpoints and all possible values disclosed between the disclosed values. The exact values of all half integral numeric values are also contemplated as specifically disclosed and as limits for all subsets of the disclosed range. For example, a range of from 0.1% to 3% specifically discloses a percentage of 0.1%, 1%, 1.5%, 2.0%, 2.5%, and 3%. Additionally, a range of 0.1 to 3% includes subsets of the original range including from 0.5% to 2.5%, from 1% to 3%, from 0.1% to 2.5%, etc. Unless stated otherwise, it will be understood that the sum of all percentages will not exceed 100%.

By "similar" it is meant that two quantities have identical or nearly identical values. For example, two similar dimensions may be within 20% or within 10% or within 5% of one another.

The apparatuses disclosed herein should be suitably dimensioned to allow for vocal fold exercises to be performed. Typically, this requires several criteria of the apparatus to be met. For example, the outer dimension of the apparatus may be small enough for a user to comfortably insert a distal end thereof in the mouth. Additionally, the outer dimension of the apparatus should be small enough to allow a user to easily carry the apparatus and hold the apparatus between the users thumb and/or one or more fingers. However, the apparatus must also have an inner dimension small enough to provide appropriate resistance to the vocal folds of a user during the vocal exercises. Exemplary inner diameters of the apparatus are between 2 mm and 6 mm (e.g., 2 mm, 3 mm, 4 mm, 5 mm, 6 mm, etc.). In most embodiments, the apparatus has a roughened surface to allow a user a grip the apparatus and/or to provide increased friction at the point of contact with the mouth. In certain implementations of the method, the user may grip the roughened surface during the vocal exercise.

A perspective view of an exemplary apparatus is illustrated in FIG. 1. Apparatus 10 is a hollow cylinder with major longitudinal axis 15. Apparatus 10 comprises the external surface 20, and internal surface 25 which run along major longitudinal axis 15. In some embodiments, the length of the apparatus along the major longitudinal axis of the cylinder is less than 20 cm (e.g., less than 15 cm, etc.). Apparatus 10 has distal ends 30 and 35 disposed at opposite ends of major longitudinal axis 15. As can be seen, apparatus 10 has a circular cross section in the plane perpendicular to the major longitudinal axis over the entire length of the apparatus. In some implementations, the axis may have a circular cross section, ovular cross section, or parallelogram cross section (e.g., rectangular cross section, square cross section, etc.). In some embodiments, the maximum outer diameter of the cross-section is less than 10 mm (e.g., less than 8 mm, less than 6 mm, less than 5 mm, etc.). In certain implementations, the maximum inner diameter of the hollow cylinder is less than 8 mm (e.g., less than 6 mm, from 2 to 6 mm, etc.). In some embodiments, the apparatus may have several contiguous portions along the major longitudinal axis, wherein each neighboring portion has different cross-sectional shape. For example, one portion may be circular, and a neighboring portion may be rectangular.

Apparatus 10 comprises roughened portion 40 which comprises ten concentric scored grips 45 around the periphery external surface 20 in a plane perpendicular to the longitudinal axis of the hollow cylinder. In some embodiments, the roughened portion comprises one or more (e.g., two, three, four, five, six, seven, eight, nine, ten, eleven, twelve, thirteen, fourteen, fifteen, etc.) concentric scored grips that extend more than 90% (e.g., more than 95%, etc.) around the periphery of the hollow cylinder in a plane perpendicular to the longitudinal axis of the hollow cylinder. In certain implementations, the roughened portion may comprise one or more ridges, grooves, scored surfaces, protrusions, or combinations thereof. The surface area of the roughened portion (e.g., the portion between furthest separated scorings, grips, grooves, or combinations thereof, etc.) may comprise less than 40% (e.g., less than 20%, less than 15%, from 5% to 15%, etc.) of the surface area of the external surface. The roughened portion percentage of the apparatus may be determined on a length basis and be represented by the length between the furthest separated scorings, grips, grooves, or combinations thereof as compared to the total length of the apparatus. Roughened portion 40 is distance 42 away from distal end 30. In some embodiments, roughened portion is at least 15% away (e.g., at least 20%, at least 25%, etc.) from one of the distal ends as measured along the longitudinal axis of the hollow cylinder. In some embodiments, the apparatus may comprise a roughened portion located at one or both distal ends of the apparatus.

The apparatuses as disclosed herein are typically reusable. The amount of reusability is often affected by the material which the apparatus is composed of. For example, the apparatus may be composed of materials with limited malleability in order to prevent deformations of the hollow cylindrical structure (particularly at the distal end). In some implementations the apparatus does not comprise or comprises less than 10% or less than 5% or less than 1% silver and/or plastic by weight of the apparatus. In some embodiments, the material comprises or is composed of nickel and/or steel and/or an elastomeric material such as silicone (e.g., polysiloxanes including silicone rubbers). In some embodiments, the apparatus comprises or is composed of stainless steel (e.g., SAE 304 stainless steel, SAE 316 stainless steel, etc.). The steel may have a gauge between 10 and 30 (e.g., gauge 18, 19, 20, 21, 22, 23, etc.). In some embodiments, the wall length of the apparatus may be less than 3 mm or less than 2 mm or less than 1.5 mm or between 0.5 and 1.5 mm.

Kits for holding the apparatus are also provided. Typically, the kit comprises:
(a) one or more (e.g., two or more, three or more, etc.) straw phonation apparatuses; and
(b) a container capable of storing the one or more apparatuses in a chamber.

The chamber may be an internal chamber in the container accessible through a port. The port may only be accessible after removal of a forcibly removable lid. In certain implementations, the container comprises one or more ventilation holes connecting the outer surface of the container to the internal chamber. These ventilation holes allow for circulating air flow around the apparatuses contained in the internal chamber. The circulating air flow may decrease the growth rates of various contaminants on the apparatuses kept in storage in the container, such as mold. In certain embodiments, the container comprises a stand such that the apparatuses are able to be held in an upright position while inserted in the container. In some embodiments, the one or more of the apparatuses are removably attached to the container, such as with magnetic interaction between the container and the apparatus or fasteners such as hook and loop fasteners configured to the container itself and adapted for holding one or more of the apparatuses.

The kit may comprise two or more (e.g., two, three, four, five, etc.) of the apparatuses. In some embodiments the kit comprises three apparatuses. In some implementations, each of the apparatuses in the kit have similar dimensions. For example, the maximum inner diameter of each of said apparatuses may be similar (e.g., within 10% of one another, etc.) and/or the maximum outer diameter of each of said apparatuses are similar (e.g., within 10% of one another, etc.) and/or the length along the major longitudinal axis of said apparatuses are similar (e.g., within 10% of one another, etc.). In certain implementations, each of the apparatuses in the kit may have an inner diameter dimension of between 2 mm and 4 mm (e.g., 2 mm, 3 mm, 4 mm, 5 mm, etc.), and/or an outer diameter of between 3 mm and 8 mm (e.g., 3 mm, 4 mm, 5 mm, 6 mm, 7 mm, 8 mm, etc.) and/or a length along the major longitudinal axis of between 5 mm and 20 mm (e.g., 10 mm, 12.5 mm, 15 mm, etc.). In some embodiments, each apparatus in the kit has a different inner diameter in order to provide a range of apparatus each providing different a resistance for the vocal fold training. In certain embodiments, each apparatus in the kit has an absolute difference in inner diameter and/or outer diameter from the other apparatuses in the kit of at least 0.75 mm or at least 0.9 mm or at least 1 mm. The kit may further comprise a wire brush from cleaning the apparatuses as well. In certain embodiments, the kit further comprises instructions. The instructions may describe methods of cleaning and storing the apparatuses and/or specific straw phonation techniques including those described herein.

The container of the kit may provide a barrier to prevent damage to the apparatuses. For example, the container may comprise, consist essentially, or consist of a hard material such as wood (e.g., bamboo) and the apparatuses may be contained in an internal chamber during storage. In these configurations, the apparatuses are may be protected by errant external forces which may have damaged the apparatuses during storage without the container. It specific implementations, the kit may comprise a container made of way with one or more ventilation holes connected to an internal chamber dimensioned to allow a user to store one or more of the apparatuses.

The apparatuses may be used for exercising the voice of a user (e.g., aligning the vocal folds of a user, etc.). In some embodiments, the method may help align and/or straighten and/or extend the vocal folds of a user. These methods may be helpful to train and develop the voice of a user. These methods may comprise:
(a) inserting the distal end of a straw phonation apparatus into the mouth of a user;
(b) forming a seal between the outer periphery of the apparatus and the mouth; and
(c) creating sound with said vocal folds (e.g., causing vocal fold vibration) while the apparatus is positioned in the mouth.

The sound may be a pitch glide in the vocal range. In certain embodiments, the sound is produced for more than 5 seconds. In some embodiments, the creating step is repeated one or more times. These sounds may be chosen specifically towards cultivating a set of vocal skills in the user. For example, the sounds may be chosen in order to train for belting, transitioning, riffing, extending range, balance and/or strength of a singer. In certain embodiments, treatment regimens are provided wherein a user is instructed to repeat the method one or more times daily (e.g., twice daily, three times daily, etc.) for a period of at least two weeks (e.g., at least three weeks, at least four weeks, at least five weeks, at least two months, etc. etc.). In some embodiments, the sound is selected from a sound exercise such as belting, transitioning, riffing, extending range, extending balance, and extending strength of the voice of a user.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications and variances which fall within the scope of the appended claims.

The invention claimed is:
1. A kit comprising:
(a) a first, second, and third apparatus for exercising the voice of a user, wherein said first apparatus, second apparatus and third apparatus are each composed of a unitary piece of material formed as a hollow cylinder; the outer diameter of said hollow cylinder is dimensioned to be gripped by said user at a location away from one or both distal ends of said hollow cylinder between a thumb and index finger of said user; one of said distal ends is dimensioned to be inserted into the mouth of said user; and a portion of said outer diameter comprises a roughened surface for said gripping by said user; and
(b) a container capable of storing said one or more apparatuses;
wherein said first apparatus has an inner diameter of 2 mm, said second apparatus has an inner diameter of 3 mm, and said third apparatus has an inner diameter of 4 mm.
2. The kit according to claim 1, wherein said container comprises an internal chamber and a lid capable of being forcibly removed to provide access to said internal chamber.

3. The kit according to claim 2, wherein said container comprises one or more ventilation holes connecting an outer surface of said container to said internal chamber.

4. The kit according to claim 1, wherein said container comprises a stand.

5. The kit according to claim 1, wherein said kit further comprises a brush for cleaning at least one of said first apparatus, said second apparatus, and third apparatus.

6. The kit according to claim 5, wherein said brush is a thin bristle wire brush.

7. The kit according to claim 1, wherein said kit further comprises instructions describing straw phonation techniques.

* * * * *